(12) United States Patent
Shimizu et al.

(10) Patent No.: US 8,241,580 B2
(45) Date of Patent: Aug. 14, 2012

(54) PLASMA PROCESSING METHODS FOR INACTIVATING TOXINS

(75) Inventors: Naohiro Shimizu, Miura (JP); Yuichiro Imanishi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/929,412

(22) Filed: Jan. 21, 2011

(65) Prior Publication Data

US 2011/0135536 A1 Jun. 9, 2011

Related U.S. Application Data

(63) Continuation of application No. 11/826,948, filed on Jul. 19, 2007, now abandoned.

(30) Foreign Application Priority Data

Dec. 27, 2006 (JP) .................................. 2006-351345

(51) Int. Cl.
*B01J 19/08* (2006.01)
(52) U.S. Cl. .............. 422/186.05; 422/186; 422/186.04; 204/156; 204/157.15; 204/164
(58) Field of Classification Search ............. 422/186.05, 422/186, 186.04; 204/156, 157.15, 164
See application file for complete search history.

(56) References Cited

U.S. PATENT DOCUMENTS

| 4,979,467 A * | 12/1990 | Kamaji et al. ............ 118/723 E |
| 5,460,802 A | 10/1995 | Asami et al. |
| 2004/0183461 A1* | 9/2004 | Kane et al. .................... 315/219 |
| 2005/0205206 A1 | 9/2005 | Lembersky |
| 2006/0070574 A1 | 4/2006 | Derderian et al. |
| 2006/0181708 A1 | 8/2006 | Takahashi et al. |

FOREIGN PATENT DOCUMENTS

| EP | 0 277 505 A1 | 8/1988 |
| JP | A-63-174658 | 7/1988 |
| JP | A-63-318947 | 12/1988 |
| JP | A-2000-295981 | 10/2000 |
| JP | A-2002-151295 | 5/2002 |
| JP | A-2002-263169 | 9/2002 |
| JP | A-2003-62047 | 3/2003 |

OTHER PUBLICATIONS

Iida, K., et al. "Inductive Energy Storage Type Power Supply for Pulse," *15th SI Device Symposium*, (2002).
Hosobuchi, K., et al. "Inactivation of Dry Endotoxin by Several Sterilization Methods," *Tokyo Metropolitan Industrial Technology Laboratory Research Report*, No. 2, pp. 126-129, (1999).

* cited by examiner

*Primary Examiner* — Jeffrey T Barton
*Assistant Examiner* — Xiuyu Tai
(74) *Attorney, Agent, or Firm* — Oliff & Berridge, PLC

(57) ABSTRACT

This invention concerns with the plasma inactivating method and processor that can inactivate the surface of the object without causing the degradation inside of it. The inactivation of toxins on the surface of the object proceeds as removing the toxins by nitriding or oxidizing the toxins by the following triple effects, the sharp pulsed electric field by the supply of the electric pulses, the generated N-radicals (N*) contained inside of the plasma in the surrounding gases composed mainly by $N_2$ gas under the low pressure.

13 Claims, 9 Drawing Sheets

FIG. 1

| GAS MOLECULE | $F_2$ | $H_2O_2$ | OH | $N_2O$ | $O_2$ | $CO_2$ | NO | $N_2$ |
|---|---|---|---|---|---|---|---|---|
| DISSOCIATION ENERGY | 1.66 | 2.21 | 4.62 | 4.93 | 5.21 | 5.52 | 6.50 | 9.91 |

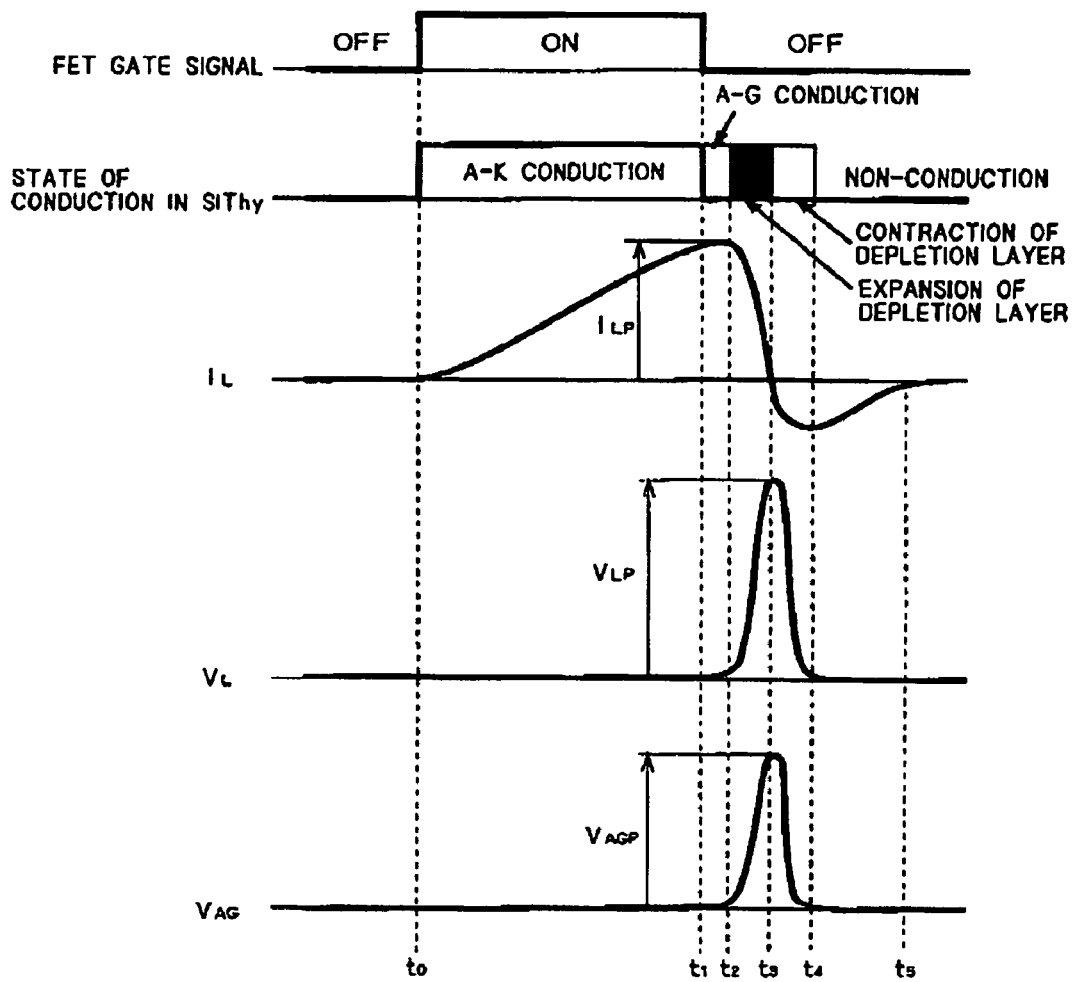

F I G . 1 0
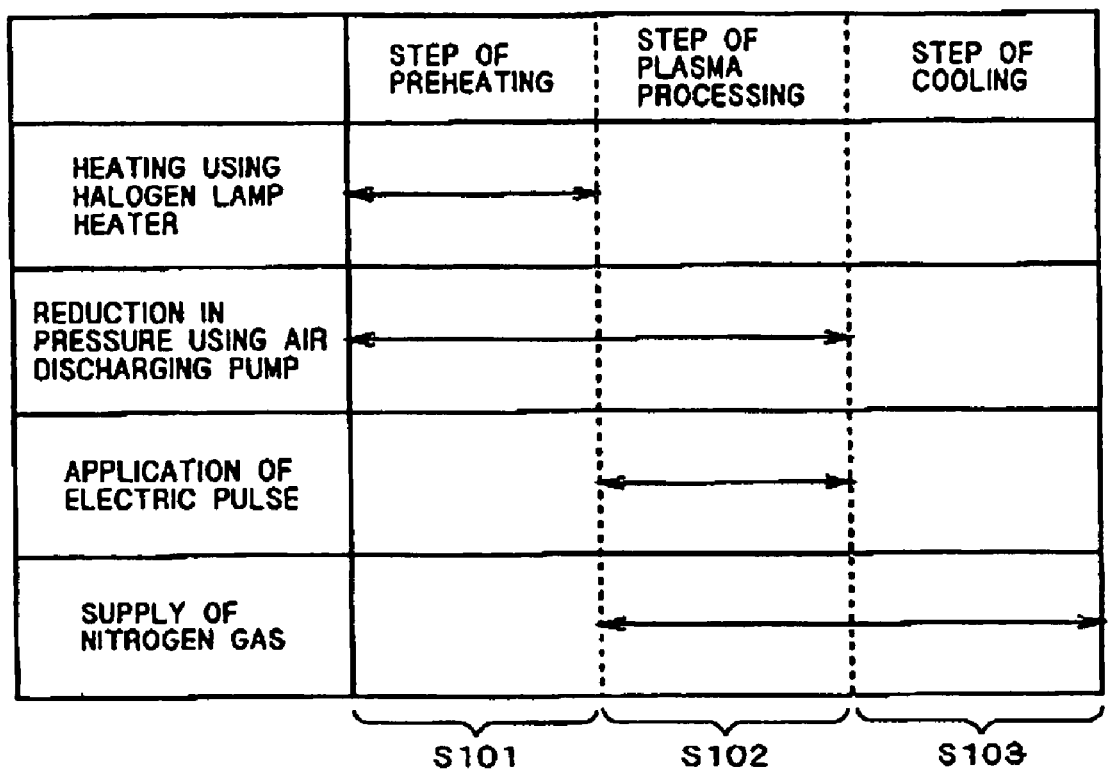

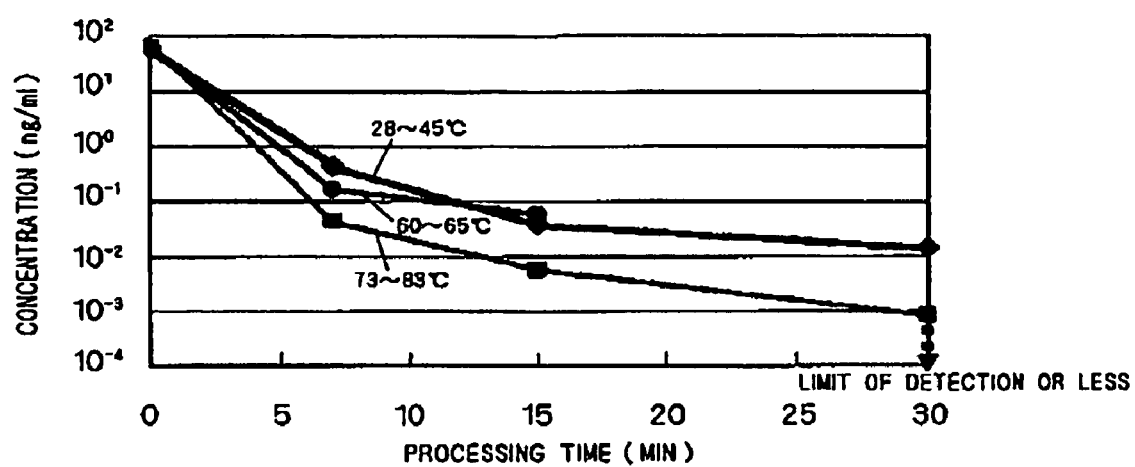
F I G . 1 1

PLASMA PROCESSING METHODS FOR INACTIVATING TOXINS

This is a Continuation of application Ser. No. 11/826,948 filed Jul. 19, 2007, which claims priority to Japanese Patent Application No. 2006-351345 filed Dec. 27, 2006. The disclosure of the prior applications are hereby incorporated by reference herein in their entireties.

This application is based on application No. JP2006-351345 filed in Japan, the contents of which are hereby incorporated by reference.

BACKGROUND OF THE INVENTION

1. Field of the Invention

The present invention relates to a plasma processing apparatus for inactivating toxins such as endotoxins and abnormal prions.

2. Description of the Background Art

Endotoxins are lipopolysaccharides which form the outer membrane of the cell wall of gram-negative bacteria. It is known that only a microscopic amount of endotoxins have heat buildup, and it is necessary to inactivate endotoxins sticking to medical tools in order to prevent medical accidents. As for methods for inactivating endotoxins, a gamma ray method, an electron beam method, an ethylene oxide gas method, a hydrogen peroxide gas plasma method, an autoclave method and a dry heat method have been examined (see, for example, Kazunari Hosofuchi et al. "Inactivation of Dry Endotoxins in Accordance with Various Sterilizing Methods," Tokyo Metropolitan Industrial Technology Laboratory Research Report, Tokyo Metropolitan Industrial Technology Laboratory, 1999, No. 2, pp. 126 to 129).

In accordance with the conventional methods other than the dry heat method, however, the activity of endotoxins cannot be sufficiently lowered. In the case where typical processing conditions are adopted, for example, the activity of endotoxins can only be lowered to approximately $1/4$ in accordance with the gamma ray method, the electron beam method or the ethylene oxide gas method, to approximately $1/20$ in accordance with the hydrogen peroxide gas plasma method, and to approximately $1/8$ in accordance with the autoclave method. Meanwhile, though the activity of end toxins can be lowered to approximately $1/10^5$ in accordance with the dry heat method, it is necessary to heat a treatment object to approximately 250° C., and therefore, there is a problem, such that the treatment object is damaged.

Here, this problem with inactivation is also present with toxins other than endotoxins such as abnormal prions, which are assumed to be toxins causing bovine spongiform encephalopathy.

BRIEF DESCRIPTION OF THE DRAWINGS

FIG. 1 is a diagram showing dissociation energy of various gas molecules;

FIG. 9 is a diagram showing an operation of the IES circuit;

FIG. 10 is an explanatory diagram illustrating operations of the plasma processing apparatus; and FIG. 11 is a diagram showing drops of activity of endotoxins.

SUMMARY OF THE INVENTION

Figure 2:
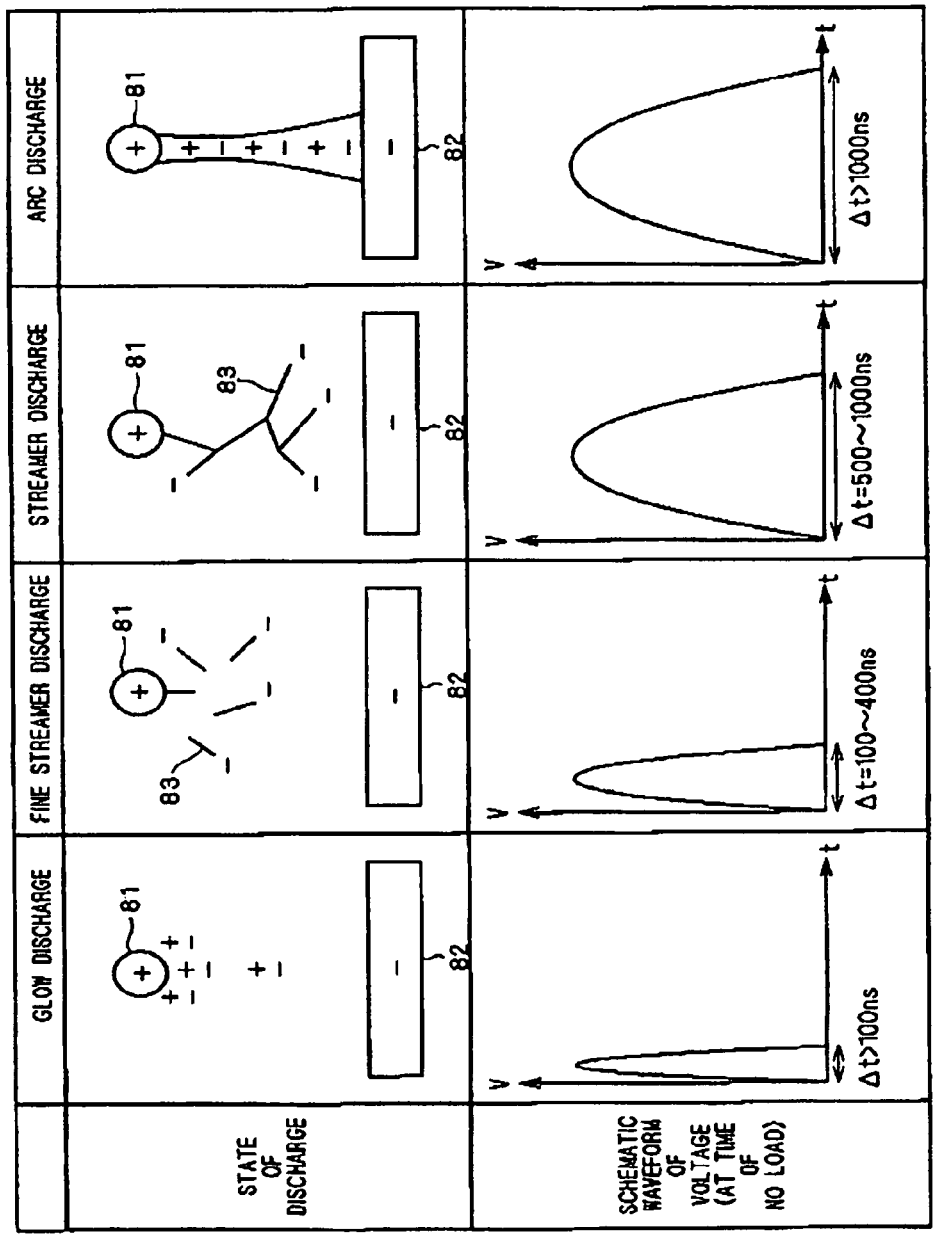
FIG. 2 is a schematic diagram illustrating discharge states and rough voltage waveforms of electric pulses.

The present invention relates to a plasma processing apparatus for inactivating toxins such as endotoxins and abnormal prions.

According to the present invention, a plasma processing apparatus for inactivating toxins sticking to the surface of a treatment object, includes: ambient gas adjusting means for adjusting ambient gas of a space, in which an inactivation process is scheduled, so as to provide a nitrogen ambient gas; an electrode pair disposed in the space; a pulse power supply for applying electric pulses repeatedly to the electrode pair, inducing fine streamer discharge without inducing arc discharge; and a reflection member for reflecting back the short wavelength ultraviolet ray into the inside of the space, the short wavelength ultraviolet ray going from the inside of the space to outside, wherein toxins are nitrided and oxidized, and toxins are removed from the surface of the treatment object, by treating toxins by applying pulse electric field generated by application of the electric pulse to the electrode pair, nitrogen radicals contained in the plasma generated in the nitrogen ambient gas due to fine streamer discharge, and short wavelength ultraviolet rays generated by the nitrogen ambient gas due to fine streamer discharge.

As a result, toxins sticking to the treatment object can be inactivated without damaging the treatment object.

Accordingly, an object of the present invention is to inactivate toxins sticking to the treatment object without damaging the treatment object.

DESCRIPTION OF THE PREFERRED EMBODIMENTS

<1 Inactivation of Toxins>

In the plasma processing apparatus according to the present invention, a pulse electric field, nitrogen radicals (N*) and ultraviolet rays including short wavelength ultraviolet rays of which the wavelength is no shorter than 100 nm and no longer than 280 nm (also referred to as "far ultraviolet rays" or "UV-C") work on toxins in a complex manner, so that the toxins are nitrided and oxidized, and removed from the surface of the treatment object.

Here, "toxins" are biologically active substances which are harmful to living things, typically endotoxins and abnormal prions. Here, a pulse electric field, nitrogen radicals and short wavelength ultraviolet rays may work both on the toxins and the surface of the treatment object, depending on the treatment object to which the toxins stick, and in some cases, this synergetic effect makes inactivation of toxins progress.

In the plasma processing apparatus according to the present invention, the treatment object to which toxins stick is placed between a pair of electrodes and an electric pulse having a sharp rise is applied to this electrode pair so that the pulse electric field having a sharp rise works on the toxins. This is an application of the knowledge that when toxins are exposed to an electric field, such a phenomenon can be observed that a polarized charge is induced on the anode side and the cathode side of the toxins so that an internal electric field which is stronger than the external electric field is generated inside the toxins, and therefore, when the toxins are exposed to a pulse electric field having a sharp rise, the potential gap between the anode side and the cathode side of the toxins can be abruptly increased, and thus, electrical impact can be applied to the toxins.

In addition, in the plasma processing apparatus according to the present invention, the treatment object to which toxins stick is put between a pair of electrodes which are installed in a nitrogen atmosphere, and an electric pulse having a sharp rise is applied to the pair of electrodes so as to cause fine streamer discharge, and thus, nitrogen radicals included in the plasma generated in the nitrogen atmosphere work on the toxins. Here, the reason why nitrogen radicals are selected as active species, that is, the reason why plasma is generated in a nitrogen atmosphere, is that activation of nitrogen radicals is significantly higher than for other active species, for example oxygen radicals. This is clear from the fact that the dissociation energy of nitrogen molecules ($N_2$) is 9.91 eV and the dissociation energy of oxygen molecules ($O_2$) is 5.21 eV, as shown in FIG. 1, where the dissociation energy of various gas molecules is listed in a table. In addition, the fact that the life of nitrogen radicals is long, the life of biradicals of triplet nitrogen ($^3\Sigma u$), for example, reaches 10 ms, is one reason why nitrogen radicals are selected as the active species. In addition, the fact that nitrogen gas is easily available at low cost and easy to handle is also one reason why nitrogen radicals are selected as the active species.

Furthermore, in the plasma processing according to the present invention, the treatment object to which toxins stick is irradiated with ultraviolet rays including short wavelength ultraviolet rays of which the wavelength is 250 nm which are generated in a nitrogen atmosphere due to fine streamer discharge, and thus, the short wavelength ultraviolet rays work on the toxins. Here, short wavelength ultraviolet rays are used because toxins are sensitive to short wavelength ultraviolet rays.

<2 Fine Streamer Discharge>

FIG. 2 is a diagram schematically showing the state of discharge caused by applying an electric pulse to a pair of electrodes 81 and 82 and schematic waveforms of the voltage of the electric pulse (at the time of no load). In FIG. 2, the schematic waveforms of the voltage of the electric pulse are shown as a graph plotting the change in the voltage V (longitudinal axis) relative to the time t (lateral axis).

As shown in FIG. 2, when the pulse width $\Delta t$ of the electric pulse reaches approximately 100 ns, secondary electrons which are released when positive ions collide with the cathode 82 ionize nitrogen molecules, and thus, glow discharge for generating new positive ions is caused.

Meanwhile, in the case where the ratio of increase in the voltage V along time dV/dt is approximately 30 to 50 kV/μs when the electric pulse rises, a streamer 83 starts growing from the anode 81 to the cathode 82 when the pulse width $\Delta t$ reaches approximately 100 ns. In addition, in the case where the pulse width $\Delta t$ is approximately 100 to 400 ns, the streamer 83 stops growing at the initial stage, where short streamers 83 are interspersed between the anode 81 and the cathode 82. Meanwhile, in the case where the pulse width $\Delta t$ is approximately 500 ns to 1000 ns, the streamer 83 grows all-out and becomes of such a state that a long and branched streamer 83 exists between the anode 81 and the cathode 82. In the plasma processing apparatus according to the present invention, fine streamer discharge gained by stopping discharge at the initial stage of growth of the streamer 83 is used, in order to prevent the streamer 83 from fully growing and electrically connecting the anode 81 and the cathode 82. This is because toxins can be uniformly inactivated when highly uniform fine streamer discharge is used.

Furthermore, when the pulse width $\Delta t$ reaches approximately 1000 ns, a localized concentration of current is created, and finally, arc discharge is caused.

In the above description, "approximately" is used for the pulse width $\Delta t$ and the range of the ratio of rise in the voltage V along time dV/dt at the time of the rise because these change depending on the concrete configuration of the plasma processing apparatus including distance between the pair of electrodes 81 and 82 and the structures of the anode 81 and the cathode 82 as well as the pressure of the nitrogen atmosphere. Accordingly, whether or not fine streamer discharge is gained should be determined not only from the pulse width $\Delta t$ and the ratio of the rise in the voltage V along time dV/dt at the time of the rise, but also by observing the actual discharge.

In addition, the conditions in the schematic waveform of the voltage in the electric pulse are "at the time of no load" because the schematic waveform of the voltage of the electric pulse which is actually applied across the pair of electrodes 81 and 82 varies together with variation in the concrete configuration of the plasma processing apparatus, including the distance between the pair of electrodes 81 and 82 and the structures of the anode 81 and the cathode 82, even when the power supply for the pulse is operated under the same conditions.

<3 General Structure of Endotoxins>

Figure 3:
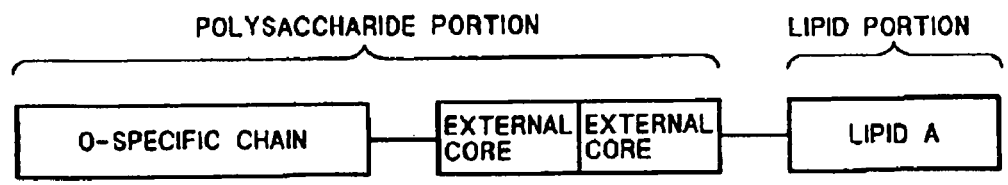
FIG. 3 is a schematic diagram illustrating a general structure of endotoxin.

FIG. 3 is a diagram schematically showing the general structure of an endotoxin which forms the outer membrane of the cell wall of a gram-negative bacterium, which is an example of a toxin. As shown in FIG. 3, the endotoxin is formed of a polysaccharide portion and a lipid portion; the polysaccharide portion is formed of an O-specific chain and cores (internal core and external core), and the lipid portion is formed of a lipid A which becomes an active portion. In the plasma processing apparatus according to the present invention, a pulse electric field, nitrogen radicals and short wavelength ultraviolet rays work on the endotoxin so that the endotoxin is nitrided and oxidized, and the endotoxin is removed from the surface of the treatment object as a gas, and thus, the endotoxin is inactivated.

Here, abnormal prions and other toxins can also be inactivated on the basis of the same principle.

<4 Example of Configuration of Plasma Processing Apparatus>

<4.1 Reactor>

Figure 4:
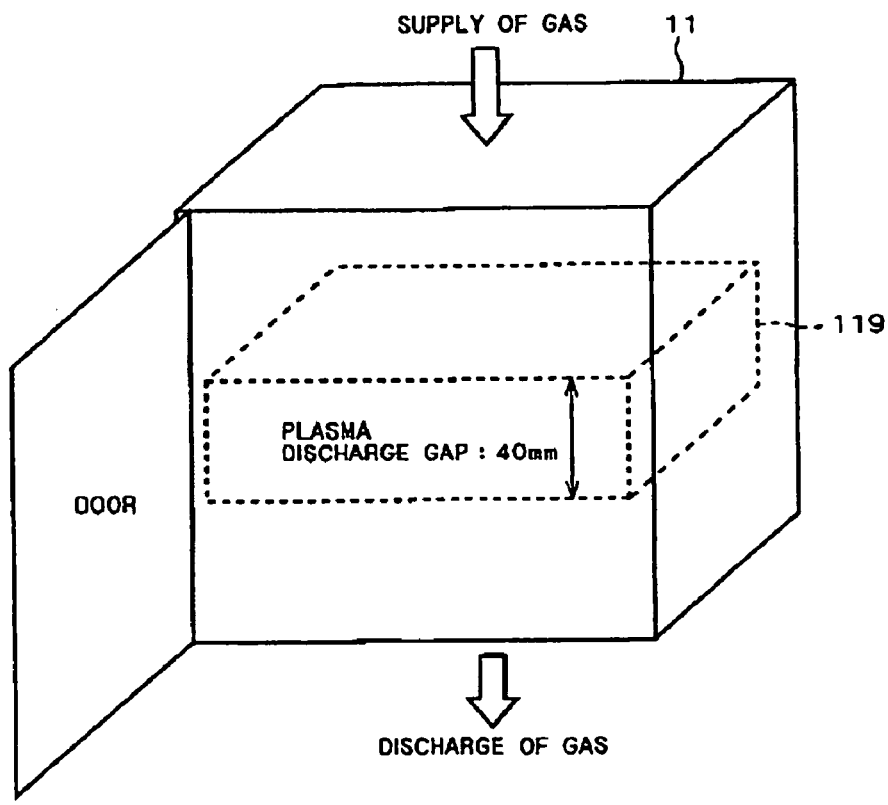
FIG. 4 is a perspective view of a reactor of a plasma processing apparatus in an embodiment.
Figure 5:
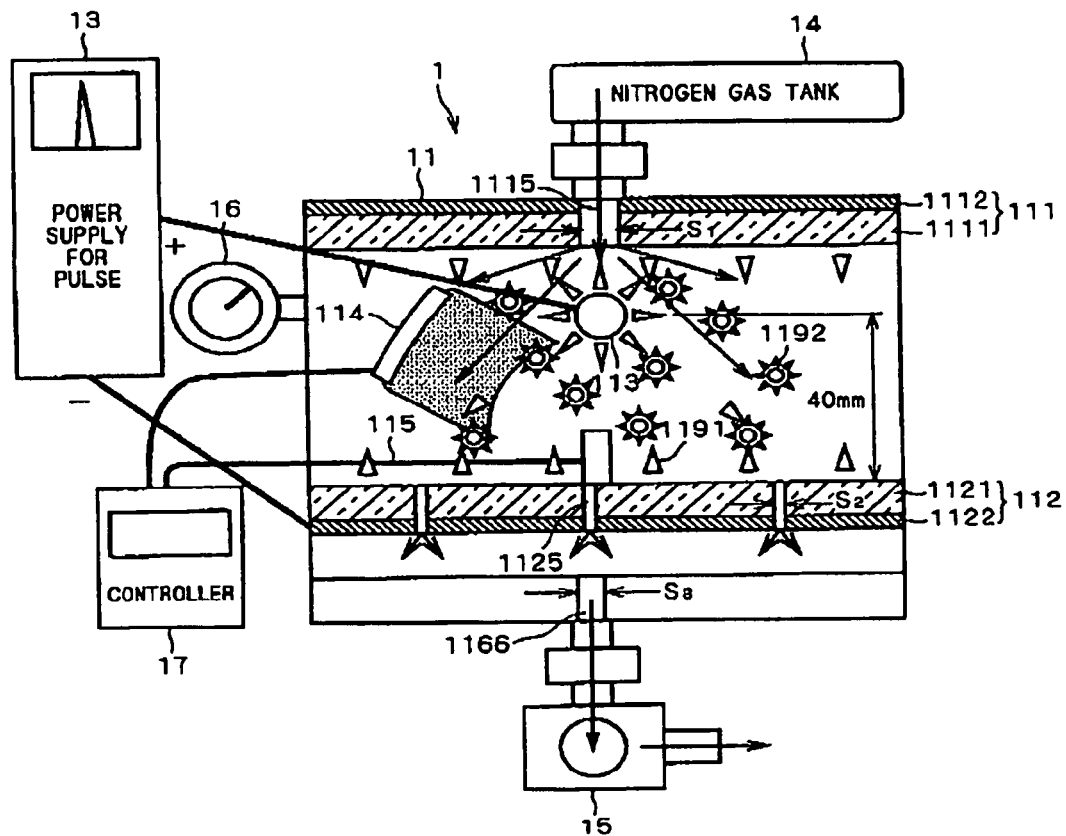
FIG. 5 is a cross-sectional view of the reactor of the plasma processing apparatus in an embodiment.

FIGS. 4 and 5 are schematic diagrams showing a reactor 11 of a plasma processing apparatus 1 according to a desirable embodiment of the present invention; FIG. 4 is a perspective diagram showing the external structure of the reactor 11, and FIG. 5 is a cross sectional diagram showing the internal structure of the reactor 11. FIG. 5 also shows attachments for the reactor 11 which forms the plasma processing apparatus 1.

As shown in FIG. 4, the reactor 11 is a batch type reaction container where a nitrogen gas is supplied through an air supplying opening on the upper side, and the nitrogen gas can be discharged from an air discharging opening on the lower aide.

An electric pulse is applied across a pair of electrodes 112 and 113 inside the reactor 11 so that plasma is generated in a plasma discharge gap 119 between the pair of electrodes 112 and 113 and a treatment object 71 is exposed to the generated plasma, and thus, toxins sticking to the treatment object 71 are inactivated.

As shown in FIG. 5, silica mirrors 111 and 112 where through holes 1115 and 1125 are created are installed horizontally at a distance in the up-down direction inside the reactor 11, and an electrode rod 113 which extends in the front-rear direction is installed horizontally between these. The power supply for a pulse 13 is connected to the pair of electrodes 112 and 113 which are formed of the silica mirror 112 which becomes the cathode and the electrode rot 113 which becomes the anode. A nitrogen gas is supplied into the reactor 11 from a nitrogen gas tank 14 through the through hole 1115, and the nitrogen gas is discharged from inside the reactor 11 through the through hole 1125 and an air discharging opening 1166 using a discharging pump 15. The pressure inside the reactor 11 can be measured using a pressure gauge 16. In addition, a halogen lamp heater 114 and an optical fiber thermometer 115 are installed inside the reactor 11. The halogen lamp heater 114 and the optical fiber thermometer 116 are connected to a controller 17.

<4.2 Silica Mirrors>

Figure 6:
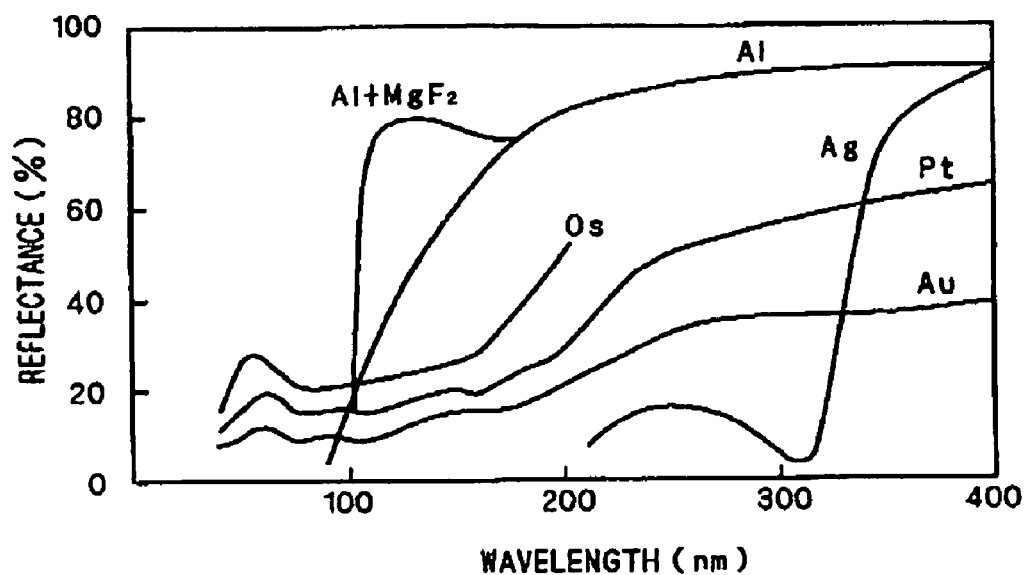
FIG. 6 is a diagram illustrating wavelength dependence of reflectivity of various metal films.

The silica mirrors 111 and 112 are made of silica glass plates 1111 and 1121 where aluminum films 1112 and 1122 are respectively vapor deposited on one of the main surfaces. The other main surface of the silica glass plates 1111 and 1121, on which the aluminum film 1112 and 1122 is not vapor deposited, faces the plasma discharge gap 119. The silica mirror 111 reflects short wavelength ultraviolet rays 1191 which go upward from inside the reactor 11 back into the reactor 11. The silica mirror 112 reflects short wavelength ultraviolet rays 1191 which go downward from inside the reactor 11 back into the reactor 11. In this manner, when a reflective member for returning short wavelength ultraviolet rays 1191 which go outward from inside the reactor 11 back into the reactor 11 is provided, the efficiency of using short wavelength ultraviolet rays 1191 emitted from the nitrogen atmosphere can be increased, so that the amount of short wavelength ultraviolet rays 1191 with which the treatment object 71 is irradiated can be increased, and therefore, the efficiency of inactivation of toxins can be increased. The mirror surface from which short wavelength ultraviolet rays 1191 are reflected is formed of an aluminum film because the reflectance of aluminum films for short wavelength ultraviolet rays is extremely high (approximately 90%), as shown in FIG. 6, which is a graph showing the dependency of the reflectance of various types of metal films on the wavelength, which can contribute to efficient inactivation of toxins.

<4.3 Electrodes>

The material for the electrode rod 113 is INCONEL (registered trademark), which has excellent resistance against plasma. Here, this does not preclude use of materials other than INCONEL (registered trademark), such as materials of which the main component is, for example, tungsten, molybdenum, manganese, titanium, chromium, zirconium, nickel, silver, iron, copper, platinum, palladium or another metal, for the electrode rod 113. Here, "metal" includes alloys which contain two or more types of metal, for example iron alloys, typically nickel alloys or stainless steel. Here, FIG. 5 shows only one electrode rod 113, but two or more electrode rods 113 may be arranged in the left-right direction with a distance in-between. In addition, it is also possible to form the anode of an electrode plate, but in this case, it is desirable to adopt an electrode plate in comb form or net form so that the opposite side can be seen through the electrode plate, and thus prevent the anode from blocking short wavelength ultraviolet rays 1191 and the treatment object 71 from not being irradiated with short wavelength ultraviolet rays 1191.

Here, though the silica mirror 112 functions as the cathode, and also as a reflective member for reflecting short wavelength ultraviolet rays 1191 in the reactor 11, this does not preclude installation of a cathode and a reflective member as independent members.

<4.4 Power Supply for Pulse>

Figure 7:
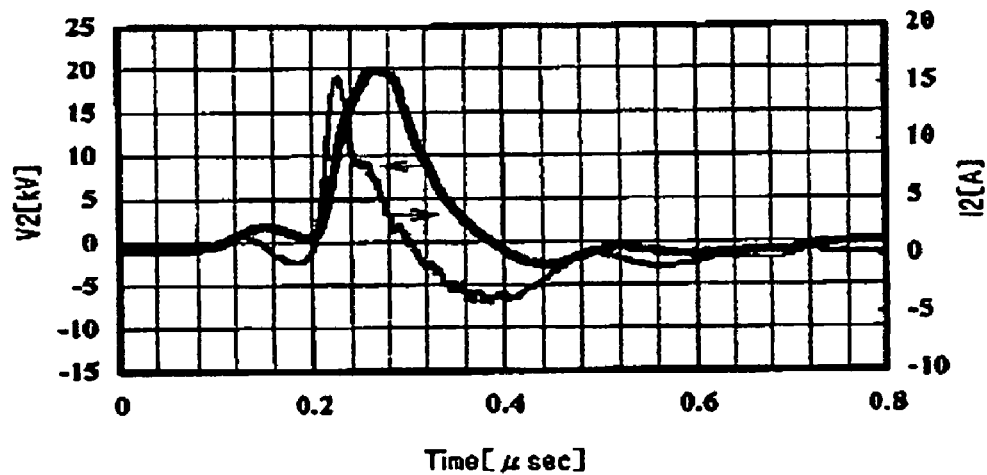
FIG. 7 is a diagram showing an example of voltage waveform and current waveform of electric pulse.

The power supply for a pulse 13 repeatedly applies an electric pulse which causes fine streamer discharge across the pair of electrodes 112 and 113 without causing arc discharge. Concretely, the power supply for a pulse 13 repeatedly applies an electric pulse of which the pulse width measured as full-width at half-maximum is 50 to 300 ns across the pair of electrodes 112 and 113. FIG. 7 shows an example of the waveform of the voltage and the waveform of the current of the electric pulse applied across the pair of electrodes 112 and 113 by the power supply for a pulse 13. FIG. 7 shows the change in a voltage V2 and a current I2 of the electric pulse (longitudinal axis) along time (lateral axis), and the pulse width measured as full-width at half-maximum is approximately 100 nm.

It is desirable to adopt an inductive energy storing type power supply circuit (hereinafter, referred to as "IES circuit") using a static induction type thyrietor (hereinafter, referred to as "SIThy") as the power supply for a pulse 13. Here, the IES circuit is described in detail in Katsuji Lida, Takeshi Sakuma, "Inductive Energy Storage Type Power Supply for Pulse," 15$^{th}$ SI Device Symposium (2002).

Figure 8:
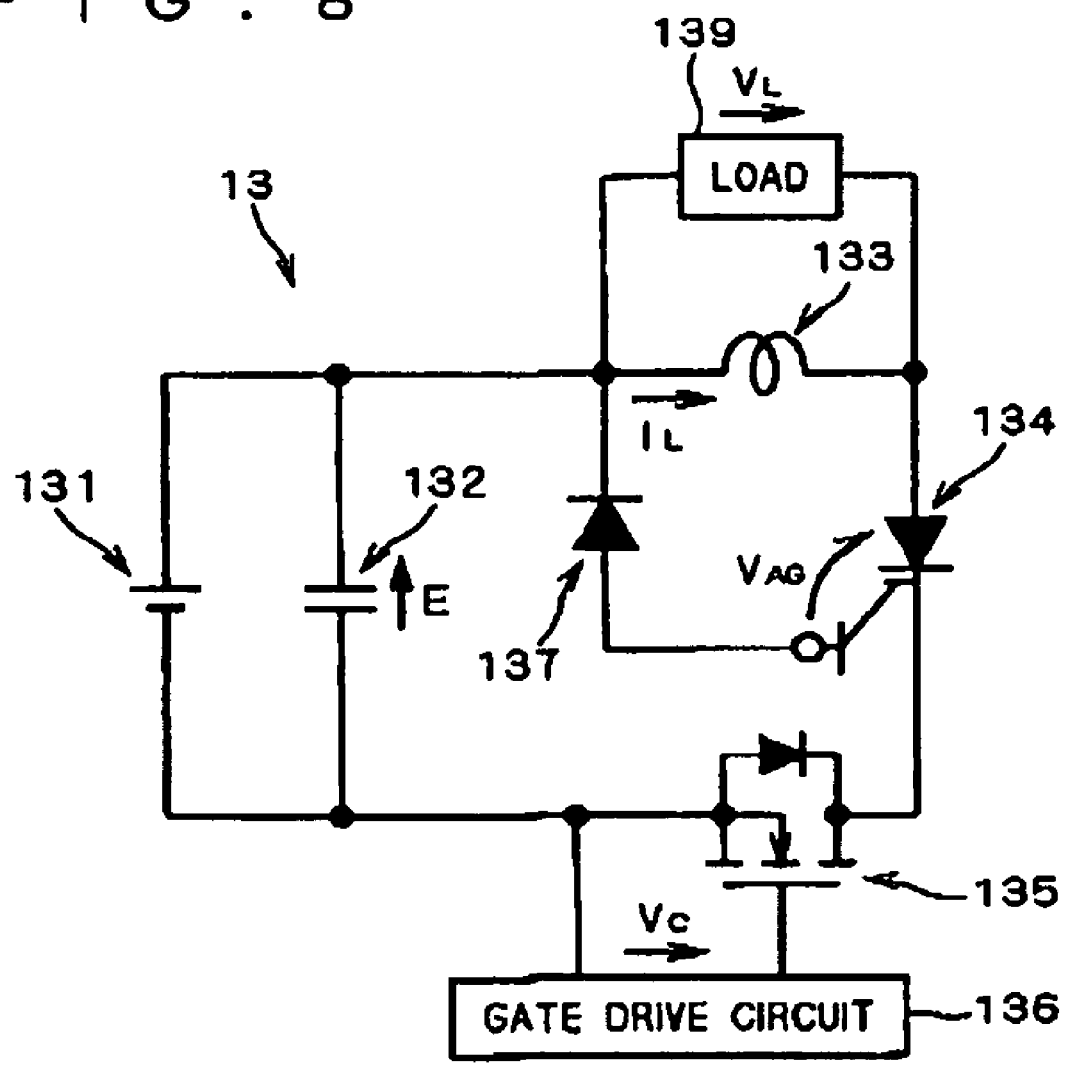
FIG. 8 is a diagram showing a structure of an IES circuit.

First, in reference to FIG. 8, the configuration of the IES circuit (power supply for a pulse) 13 is described. The IES circuit 13 includes a low voltage direct current power supply 131. A voltage E of the low voltage direct current power supply 131 may be much lower than the peak value of the voltage of the electric pulse generated by the IES circuit 13. Even in the case where a peak value $V_{LP}$ of a voltage $V_L$ generated at both ends of the below described inductor 133 reaches several kV, for example, the voltage E of the low voltage direct current power supply 131 may be several tens of V. The lower limit of the voltage E is determined to be no lower than the latching voltage of a below described SIThy 134. The IES circuit 13 can use the low voltage direct current power supply 131 as an electric energy source, and therefore, can be made compact and low-cost.

The IES circuit 13 is provided with a capacitor 132 which is connected in parallel with the low voltage direct current power supply 131. The capacitor 132 lowers the apparent impedance of the low voltage direct current power supply 131, and thus strengthens the discharge ability of the low voltage direct current power supply 131.

Furthermore, the IES circuit 13 is provided with the inductor 133, the SIThy 134, a MOSFET (Metal Oxide Semiconductor Field Effect Transistor) (hereinafter, referred to as "FET") 135, a gate drive circuit 136 and a diode 137. In the IES circuit 13, the positive electrode of the low voltage direct current power supply 131 and one end of the inductor 133 are connected, the other end of the inductor 133 and the anode of the SIThy 134 are connected, the cathode of the SIThy 134 and the drain of the FET 135 are connected, and the source of the FET 135 and the negative electrode of the low voltage direct current power supply 131 are connected. In addition, in the IES circuit 13, the gate of the SIThy 134 and the anode of the diode 137 are connected, and the cathode of the diode 137 and one end of the inductor 133 (positive electrode of the low voltage direct current power supply 131) are connected. The gate drive circuit 136 is connected to the gate and the source of the FET 135.

The SIThy 134 can be turned on and off in response to the gate signal.

The FET 135 is a switching element of which the state of conduction between the drain and the source changes in response to a gate signal $V_C$ supplied from the gate drive circuit 136. It is desirable for the on voltage or on resistance of the FET 135 to be low. In addition, it is required for the withstand voltage of the FET 135 to be higher than the voltage E of the low voltage direct current power supply 131.

The diode 137 is provided in order to block the current which flows in the case where a positive bias is applied to the gate of the SIThy 134, that is, to prevent the SIThy 134 from being driven by a current in the case where a positive bias is applied to the gate of the SIThy 134.

The inductor 133 functions as an inductive element having self-inductance, and a load 139 (here, the pair of electrodes 112 and 113) are connected in parallel to the two ends. Hero, the primary side of a boosting transformer is used as the inductor 133, and the load 139 can be connected to the two ends on the secondary side of the boosting transformer so that an electric pulse of which the peak value of the voltage is higher can be gained.

Next, the operation of the IES circuit 13 is described in reference to FIG. 9. FIG. 9 shows the gate signal $V_C$ supplied to the FET 135, the state of conductance of the SIThy 134, a current $I_L$ which flows through the inductor 133, the voltage $V_L$ across the two ends of the inductor 133 and the change in a voltage $V_{AG}$ between the anode and the gate of the SIThy 134 (longitudinal axis) along time (lateral axis) in this order from the top.

First, when the gate signal $V_C$ is switched from off to on at time $t_0$, a state of conduction is gained between the drain and the source of the FET 135. As a result, the gate of the SIThy 134 is biased positive relative to the anode, and therefore, a state of conduction is gained between the anode and the cathode of the SIThy 134 ("A-K conduction" in the figure), and the current $I_L$ starts increasing.

When the gate signal $V_C$ is switched from on to off at time $t_1$, which is around the time when the current $I_L$ reaches a peak value $I_{LP}$, a state of non-conduction is gained between the drain and the source of the FET 135, and a state of conduction is gained between the anode and the gate of the SIThy 134 ("A-G conduction" in the figure). As a result, the current $I_L$ decreases in sync with the expansion of the depletion layer in the SIThy 134 between time $t_2$ and time $t_3$ ("expansion of depletion layer" in the figure), and at the same time, the voltage $V_L$ and the voltage $V_{AG}$ abruptly rise.

In addition, after the voltage $V_L$ and the voltage $V_{AG}$ reach the peak value $V_{LP}$ and the peak value $V_{AGP}$, respectively, at time $t_3$, and the direction of the current $I_L$ is reversed, the current $I_L$ increases in sync with contraction of the depletion layer in the SIThy 134 between time $t_3$ and time $t_4$ ("contraction of depletion layer" in the figure), and at the same time, the voltage $V_L$ and the voltage $V_{AG}$ abruptly lower.

In addition, when the SIThy 134 becomes of a state of non-conduction at time $t_4$ ("non-conduction" in the figure), the current $I_L$ decreases as the time approaches time $t_5$, and at the same time, the voltage $V_L$ and the voltage $V_{AG}$ become 0.

<4.5 Adjustment of Temperature>

The controller 17 monitors the temperature of the nitrogen atmosphere using the optical fiber thermometer 115 and controls the power supplied to the halogen lamp heater 114, and thus, adjusts the temperature of the nitrogen atmosphere. As a result, the temperature of the nitrogen atmosphere can be made appropriate for inactivation, and therefore, toxins sticking to the treatment object 71 can be efficiently inactivated. A ceramic heater or the like can, of course, be used instead of the halogen lamp heater 114. Here, when the silica mirror 112, where a silica glass plate 1121 which functions as a dielectric barrier is coated with an aluminum film 1122, is used as a cathode, the time it takes for the current to stop after an electric pulse is applied across the pair of electrodes 112 and 113 becomes longer than in the case where a metal plate which is not coated with a silica glass plate 1121 is used as the cathode. Accordingly, when the silica mirror 112, where an aluminum film 1122 is coated with a silica glass plate 1121 is used as the cathode, the inputted power when an electric pulse is applied across the pair of electrodes 112 and 113 becomes greater than in the case where a metal plate which is not coated with a silica glass plate 1121 is used as the cathode, and therefore, the temperature in the nitrogen atmosphere can be increased by applying an electric pulse across the pair of electrodes 112 and 113.

<4.6 Adjustment of Atmosphere>

In the reactor 11, a nitrogen gas is supplied from the electrode rod 113 side, which becomes the anode, and the nitrogen gas is discharged from the silica mirror 112 aide, which becomes the cathode, and thus, the atmosphere inside the reactor 11 is adjusted to a nitrogen atmosphere. Nitrogen gas is supplied and discharged in this manner because a nitrogen gas flow directed to the cathode from the anode can be created parallel to the pulse electric field, and therefore, plasma can be uniformly generated, so that toxins sticking to the treatment object 71 can be inactivated uniformly. In addition, there are advantages with creating such a nitrogen gas flow, such that it becomes difficult for oxygen gas to be mixed in, preventing ozone from being generated to such an extent that no practical problems are caused, and the distance between the pair of electrodes 112 and 113 can be increased, so that toxins sticking to three-dimensional treatment object 71 can be inactivated. Here, in the case where nitrogen gas is supplied through a number of through holes 1115, it is desirable for nitrogen gas which passes through a pressure loss member mounted on the top surface of the silica mirror 111, for example layered metal nets or a porous body of ceramics, such as alumina or SiC, to be blow out through the through holes 1115. This is in order to prevent the nitrogen gas from being blown out only through the through holes 1115 in the vicinity of the air supplying opening and inactivation of toxins from becoming non-uniform.

Furthermore, the pressure inside the reactor 11 is reduced to 10,000 to 50,000 Pa (¹⁄₁₀ to ½ of atmospheric pressure), more desirably to 20,000 to 40,000 Pa, using an air discharging pump 15 so that the distance between the pair of electrodes 112 and 113 can be increased (typically five times or more than in the case of atmospheric pressure) and toxins sticking to three-dimensional objects of treatment 71 can be inactivated. Such fine streamer discharge caused under reduced pressure contributes to prolonging the life of nitrogen radicals 1192 (typically ten times or more than in the case of atmospheric pressure) and efficient inactivation of toxins sticking to the treatment object 71. Here, in order to maintain an appropriate pressure in the nitrogen atmosphere, prevent chemical species created through reaction of the nitrogen radicals 1192 from remaining, and appropriately discharge the chemical species through the plasma discharge gap 119, it is desirable for the total hole area Ss of the through holes 1125 to be greater than a total hole area $S_1$ of the through holes 1115, as well as for a total hole area $S_3$ of the air discharging openings 1166 to be greater than a total hole area $S_3$ of the through holes 1125.

<5 Operation of Plasma Processing Apparatus>

FIG. 10 is a diagram for illustrating the operation of the plasma processing apparatus 1. FIG. 10 is a diagram showing whether or not heating using the halogen lamp heater 114 is carried out, whether or not discharge using the air discharging pump 15 is carried out, whether or not application of an electric pulse across the pair of electrodes 112 and 113 is carried out, and whether or not a nitrogen gas is supplied for each of the step of preheating S101, the step of plasma processing S102 and the stop of cooling S103.

When the door is opened and the treatment object 71 is placed on the silica mirror 112 and the door closed again, the plasma processing apparatus 1 starts the step of preheating S101. In the step of preheating S101, heating using a halogen lamp heater 114 and discharging of gas using an air discharging pump 15 are carried out, so that the inside of the reactor 11 is heated.

In the subsequent step of plasma processing S102, heating using the halogen lamp heater 114 is stopped and discharging of gas using the air discharging pump 15 continues, while application of an electric pulse across the pair of electrodes 112 and 113 and supply of a nitrogen gas are started. Heating using the halogen lamp heater 114 is stopped in the step of plasma processing S102 because the temperature in the nitrogen atmosphere can be maintained even when heating is stopped, because of the input of power through application of the electric pulse. In addition, discharging of gas using the air discharging pump 15 continues so that a state where the pressure inside the reactor 11 is reduced can be maintained and a nitrogen gas flow can be created parallel to the pulse electric field. In the step of inactivation, a relatively small amount of nitrogen gas is supplied into the reactor 11, and the atmosphere inside the reactor 11 is adjusted to a nitrogen atmosphere. In addition, plasma processing is carried out on the treatment object 71 using the plasma generated in the plasma discharge gap 119 so that the pulse electric field generated through application of an electric pulse across the pair of electrodes 112 and 113, nitrogen radicals 1192 included in the plasma generated in the plasma discharge gap in the nitrogen atmosphere due to the fine streamer discharge, and short wavelength ultraviolet rays 1191 emitted from the nitrogen atmosphere due to the fine streamer discharge work on toxins sticking to the treatment object 71, and thus, the toxins are nitrided and oxidized, and removed from the surface of the treatment object 71. As a result, in the plasma processing apparatus 1, toxins sticking to the treatment object 71 can be inactivated without damaging the treatment object 71.

In the subsequent step of cooling S103, application of an electric pulse across the pair of electrodes 112 and 113 and discharging of gas using the air discharging pump 15 are stopped, while supply of a nitrogen gas continues. In the step of cooling S103, a relatively large amount of nitrogen gas is supplied into the reactor 11 and the inside of the reactor 11 is cooled. In this step of cooling S103, it becomes possible to safely remove the treatment object 71 from inside the reactor 11.

EXAMPLE

In the present example, in the plasma processing apparatus 1, an electric pulse where the peak value of the voltage was 19.0 kV and the frequency was 2.5 kHz was applied across the pair of electrodes 112 and 113, and the reduction in the activity of endotoxins as a result of plasma processing under reduced pressure was evaluated while the temperature of the nitrogen atmosphere and the processing time for plasma processing were changed. "Lipopolysaccharides from *Escherichia Coli* 0111" made by Sigma Aldrich Japan K. K. was selected as an endotoxin, and "Limulus ES-II Test Wako" made by Wako Pure Chemical Industries, Ltd. was selected as a limulus reagent, and the activity of the endotoxin was measured using "Toxinometer ET-2000/J" made by Wako Pure Chemical Industries, Ltd. FIG. 11 shows the results. FIG. 11 shows the change in the concentration (longitudinal axis) of the endotoxin in the specimen along the processing time (lateral axis) for plasma processing for respective temperature ranges in the nitrogen atmosphere (28 to 45° C., 60 to 65° C., and 73 to 83° C.). Here, the amount of flow of the nitrogen gas was 6 liter/min. In addition, the inputted power was 84 W.

As shown in FIG. 11, the higher the temperature in the nitrogen atmosphere became and the longer the processing time for plasma processing became, the lower the concentration of the endotoxin became. When the processing time for plasma processing was approximately 7 minutes, the concentration of the endotoxin lowered to below $10^{-1}$ to $10^0$ ng/ml, which is a lethal dose for humans, and when the temperature in the nitrogen atmosphere was 73 to 83° C. and the processing time for plasma processing was 30 minutes, the concentration of the endotoxin lowered to below $10^{-3}$ ng/ml, which is the limit of detection. That is, the plasma processing apparatus 1 of the present invention allows endotoxins to be completely inactivated in a short period of time at a much lower temperature than for a dry heat method, and therefore, endotoxins sticking to the treatment object 71 can be completely inactivated without damaging the treatment object 71.

What is claimed is:

1. A plasma processing method for inactivating toxins sticking to the surface of a treatment object, comprising steps of:
    (a) providing an ambient gas adjuster;
    (b) providing an electrode pair disposed in a space, said electrode pair comprising an anode and a cathode;
    (c) providing a pulse power supply;
    (d) providing a reflection member;
    (e) making said ambient gas adjuster to supply nitrogen gas from said anode side and to exhaust nitrogen gas from said cathode side, generating a nitrogen gas flow and adjusting ambient gas of the space in which an inactivation process is scheduled;
    (f) making said pulse power supply to apply electric pulses repeatedly to said electrode pair, generating a pulse electric field parallel to said nitrogen gas flow, inducing fine streamer discharge without inducing arc discharge, and stopping the discharge at an initial stage of growth of a streamer;
    (g) making said reflection member to reflect back short wavelength ultraviolet ray into inside of the space, said short wavelength ultraviolet ray being emitted by nitrogen ambient gas due to fine streamer discharge and going from the inside of the space to outside;
    (h) applying pulse electric field to toxins, the pulse electric field being generated by application of the electric pulse to said electrode pair;
    (i) applying nitrogen radicals to toxins, the nitrogen radicals being contained in the plasma generated in the nitrogen ambient gas due to fine streamer discharge;
    (j) applying short wavelength ultraviolet rays to toxins, short wavelength ultraviolet rays being generated by the nitrogen ambient gas due to fine streamer discharge; and
    (k) nitriding and oxidizing toxins by said steps (h), (i) and (j) so as to be removed from the surface of the treatment object.

2. The plasma processing method according to claim 1, wherein the toxins are endotoxin or abnormal prion.

3. The plasma processing method according to claim 1, wherein the half width of pulse width of electric pulse is 50 to 300 ns.

4. The plasma processing method according to claim 1, wherein the ambient gas adjuster includes an evacuator that evacuates the space.

5. The plasma processing method according to claim 1, further comprising steps of:
(l) providing a temperature adjuster; and
(m) making said temperature adjuster adjust the temperature of the nitrogen ambient gas.

6. The plasma processing method according to claim 1, wherein said reflection member reflects short wavelength ultraviolet rays by an aluminum film.

7. The plasma processing method according to claim 1, wherein the step of making said pulse power supply to apply electric pulses repeatedly to said electrode pair is carried out such that the ratio of increase in voltage V along time dV/dt is approximately 30 to 50 kV/μs when the electric pulse rises.

8. The plasma processing method according to claim 1, wherein the fine streamer discharge is induced under reduced pressure conditions in the range of from 10,000 to 50,000 Pa.

9. The plasma processing method according to claim 1, wherein the reduced pressure conditions are the range of from 20,000 to 40,000 Pa.

10. The plasma processing method according to claim 1, wherein the pulse power supply comprises an inductive energy storing type power supply circuit using a static induction type thyrietor, and the inductive energy storing type power supply circuit includes a low voltage direct current power supply.

11. The plasma processing method according to claim 7, wherein the inductive energy storing type power supply circuit further comprises a capacitor, an inductor, and a metal oxide semiconductor field effect transistor having a source and drain; wherein
the capacitor is connected in parallel with the low voltage direct current power supply,
a positive electrode of the low voltage direct current power supply and one end of the inductor are connected,
a anode of the static induction type thyrietor and the other end of the inductor are connected,
a cathode of the static induction type thyrietor and the drain of the metal oxide semiconductor field effect transistor are connected, and
the source of the metal oxide semiconductor field effect transistor and a negative electrode of the low voltage direct current power supply are connected.

12. The plasma processing method according to claim 8, wherein the inductive energy storing type power supply circuit further comprises a gate drive circuit, and a diode; wherein
a gate of the static induction type thyrietor and an anode of the diode are connected,
a cathode of the diode and the end of the inductor connected to the positive electrode of the low voltage direct current power supply are connected, and
the gate drive circuit is connected to a gate and the source of the metal oxide semiconductor field effect transistor.

13. The plasma processing method according to claim 1, wherein the step of inducing fine streamer discharge without inducing arc discharge occurs at a temperature of in the range of from 73° C. to 83° C.

* * * * *